United States Patent [19]

Nishimura et al.

[11] 3,970,677

[45] July 20, 1976

[54] METHOD FOR ISOLATING 11-CYANO-UNDECANOIC ACID IN ITS AMMONIUM SALT

[75] Inventors: Kenji Nishimura; Shinichi Furusaki; Kazuo Hashimoto, all of Ube, Japan

[73] Assignee: Ube Industries, Ltd., Tokyo, Japan

[22] Filed: Jan. 23, 1975

[21] Appl. No.: 543,445

[30] Foreign Application Priority Data

Feb. 1, 1974 Japan................................. 49-12717

[52] U.S. Cl................................ 260/404.5; 260/404
[51] Int. Cl.$^2$.................................... C07C 121/407
[58] Field of Search......................... 260/404, 404.5

[56] References Cited
UNITED STATES PATENTS 3,217,027  11/1965  Little .............................. 260/404 X Primary Examiner—Patrick P. Garvin

[57] ABSTRACT

11-cyano-undecanoic acid is isolated in its ammonium salt in a high purity from a crude material by the method wherein the crude material containing 11-cyano-undecanoic acid is dissolved in an organic solvent consisting of one or more aromatic hydrocarbons having 6 to 8 carbon atoms, ammonium gas is introduced into the crude material solution to convert the dissolved 11-cyano-undecanoic acid its ammonium salt, crystals and, thereafter, the crystals of ammonium salt are separated from the solution.

8 Claims, No Drawings

METHOD FOR ISOLATING 11-CYANO-UNDECANOIC ACID IN ITS AMMONIUM SALT

The present invention relates to a method for isolating 11-cyano-undecanoic acid salt from a crude material and, more particularly, relates to a method for isolating the ammonium salt of 11-cyano-undecanoic acid from a crude material.

11-cyano-undecanoic acid is useful as an intermediate material for producing polymeric materials. For example, 11-cyano-undecanoic acid is converted to 12-aminododecanoic acid by hydrogenation, and 12-aminododecanoic acid can be polymerized to produce nylon 12.

British Patent No. 1,198,422 discloses a method for producing 11-cyano-undecanoic acid by thermally cracking 1,1′-peroxy-dicyclohexylamine at a high temperature of 300° to 1000°C. German published Application No. 2,038,956 discloses an improved method for producing 11-cyano-undecanoic acid by carrying out the thermal cracking method of the British Patent while an inert gas is introduced into the thermal cracking system.

The crude oily material produced by the method of the British Patent method and the German published Application, contains therein 11-cyano-undecanoic acid in an amount corresponding to 50 to 60% of the weight of the thermally cracked 1,1′-peroxy-dicyclohexylamine, ε-caprolactam in an amount corresponding to 10 to 20% thereof, cyclohexanone in an amount corresponding to 10 to 20% thereof and other by-products (including saturated and unsaturated carboxylic acids, nitriles and cyclic imides) in an amount corresponding to 10 to 20% thereof. Generally, the crude oily material is dark brown or brownish black. Accordingly, in order to obtain 11-cyano-undecanoic acid which is usable as a material for the chemical industry, it is required that 11-cyano-undecanoic acid having impurities and coloring substances in an amount as small as possible be isolated with a high recovery yield from the crude oily material containing a large amount of impurities and coloring and substances.

In conventional methods for recovering 11-cyano-undecanoic acid from the crude oily material, the crude oily material is subjected to distillation. However, as 11-cyano-undecanoic acid has low volatility and poor thermal stability, a large amount of 11-cyano-undecanoic acid is thermally decomposed during the distillation period. This results in low recovery yield of 11-cyano-undecanoic acid. Further, since the crude oily material contains impurities having a boiling point close to that of 11-cyano-undecanoic acid, it is difficult to obtain high purity 11-cyano-undecanoic acid.

British Patent No. 1,289,680 discloses a method for isolating refined 11-cyano-undecanoic acid in the form of solid particles by spraying a crude 11-cyano-undecanoic acid which has been melted or dissolved in a solvent miscible with water, into water or water containing the solvent therein. According to the British Patent method, 11-cyano-undecanoic acid can be recovered quantitatively from the crude material. However, the British Patent method has a disadvantage in that the refined 11-cyano-undecanoic acid still contains a relatively large amount of impurities, particularly, colored substances. This disadvantage will be illustrated in Comparative Example 4 hereinafter.

Also, British Patent No. 1,266,213 discloses a method for isolating 11-cyano-undecanoic acid by dissolving a crude oily material in a solvent containing ammonia in order to convert 11-cyano-undecanoic acid to its ammonium salt, crystallizing the ammonium salt from the solvent by cooling and, then, separating the crystallized ammonium salt from the solvent. In the British Patent method, it is required that the solvent containing ammonia be capable of dissolving the ammonium salt of 11-cyano-undecanoic acid at a high temperature, and be capable of allowing the cyrstallization of the ammonium salt at a low temperature. A solvent having the above-mentioned capabilities and usable in the chemical industry is an aqueous ammonia solution. This method can provide for recovery of 11-cyano-undecanoic acid having a relatively high purity. However, since the aqueous ammonia solution has a relatively high solubility for the ammonium salt of 11-cyano-undecanoic acid even at a low temperature of, for example, 10°C or lower, there is a disadvantage since the recovery or yield of the ammonium salt is not sufficiently high. This disadvantage will be illustrated hereinafter in Comparative Example 5. Further, the British Patent method has the following other disadvantage. The impurities and the coloring substances in the crude material are concentrated into the aqueous ammonia solution separated from the crystallized ammonium salt of 11-cyano-undecanoic acid when the aqueous ammonia solution is repeatedly used as a solvent for the crude material. The concentrated impurities and coloring substances undesirably affect the crystallization velocity, recovery or yield and quality of the ammonium salt of 11-cyano-undecanoic acid. The British Patent also discloses another solvent consisting of water-saturated chloroform. However, the water-saturated chloroform has a lower solubility for the ammonium salt of 11-cyano-undecanoic acid than that of the aqueous ammonium solution. Accordingly, the amount of the water-saturated chloroform solvent necessary for dissolving the fixed amount of the ammonium salt of 11-cyano-undecanoic acid is remarkably larger than that of the aqueous ammonia solution. This result is an economical disadvantage. The water-saturated chloroform also creates a disadvantage in that the ammonium salt is crystallized as particles having a very small size from the solvent and, therefore, the filtration of the crystallized ammonium salt is difficult and requires a very long time. Further, the yield of the ammonium salt is not sufficiently high. These disadvantages will be illustrated hereinafter in Comparative Example 6.

The object of the present invention is to provide a method for isolating 11-cyano-undecanoic acid in the form of its ammonium salt containing therein either none or, at most a very small amount of impurities and coloring substances, and to accomplish this from a crude material with a high recovery or yield.

The above yield can be accomplished by the method of the present invention which comprises the steps of:
dissolving a crude material containing therein 11-cyano-undecanoic acid into an organic solvent consisting of at least one aromatic hydrocarbon having 6 to 8 carbon atoms;
introducing ammonia gas into the above-prepared solution to convert the dissolved 11-cyano-undecanoic acid to its ammonium salt crystals and;
separating said crystals of ammonium salt of 11-cyano-undecanoic acid from said solution.

The method of the present invention is characterized in that the organic solvent consisting of at least one aromatic hydrocarbon having 6 to 8 carbon atoms is used to dissolve the crude material, containing therein 11-cyano-undecanoic acid, and ammonia in the gaseous state is introduced into the solution. The special solvent of the present invention can dissolve 11-cyano-undecanoic acid, but not its ammonium salt. In the special solvent of the present invention, the 11-cyano-undecanoic acid is converted into its ammonium salt, and the resultant ammonium salt thereof is crystallized immediately when conversion starts and precipitated from the liquid phase solution. The crystallization of the ammonium salt of 11-cyano-undecanoic acid is effected at a high crystallizing velocity and the resultant crystals have a desirable large size for filtration and contain therein none, or at most a very small amount of impurities and coloring substances. The method of the present invention is beneficially applied to a crude oil prepared by thermally cracking 1,1'-peroxy-dicyclohexylamine at a temperature of 300° to 1000°C. In the thermal cracking, about 50 to 60% by weight of 1,1'-peroxy-dicyclohexylamine is converted to 11-cyano-undecanoic acid.

The aromatic hydrocarbon usable as the solvent for the method of the present invention can be selected from the group consisting of benzene, toluene, xylene, ethyl benzene and mixtures of two or more of the above-mentioned compounds. When an aromatic hydrocarbon having more than 8 carbon atoms is used as a solvent, the larger the number of carbon atoms in the aromatic hydrocarbon the larger the amount of the impurities contained in the crystallized ammonium salt of 11-cyano-undecanoic acid. Some alicyclic hydrocarbons, for example, cyclo-hexane, and some aliphatic hydrocarbons, for example, n-hexane, are also able to dissolve the crude material containing 11-cyano-undecanoic acid to some extent but not to dissolve its ammonium salt. However, these hydrocarbons undesirably tend to introduce a large amount of impurities, for example, ε-caprolactan, and colored substances into the crystallized ammonium salt of 11-cyano-undecanoic acid from the hydrocarbons. If other solvents, for example, chloroform, are used in place of the special aromatic hydrocarbon, the crystallization of the ammonium salt of 11-cyano-undecanoic acid from the other solvents results in very small size crystals and a low recovery yield.

Compared with the other solvents, the solvent of the present invention can allow the ammonium salt of 11-cyano-undecanoic acid to selectively crystallize with a relatively large crystal size at about room temperature, at which the solubility of the ammonium salt in the special aromatic hydrocarbon solvent is sufficiently low. Accordingly, a high purity ammonium salt of 11-cyano-undecanoic acid can be easily separated from the solvent with a high recovery yield by way of filtration.

In the method of the present invention, it is preferable that the crude material be dissolved in the special solvent of the present invention in such a manner that the concentration of 11-cyano-undecanoic acid in the solution becomes between 5 and 30%, more preferably, 7 and 15% by weight. If more than 30% by weight of 11-cyano-undecanoic acid is contained in the solution, it tends to be difficult to filter the slurry wherein a large amount of the resultant crystals is suspended and the resultant crystals tend to contain therein a relatively large amount of colored substances. A concentration lower than 5% by weight of 11-cyano-undecanoic acid results in an economic disadvantage.

The solution of the crude material in the organic solvent preferably contains as little water as possible, particularly, less than 3% by weight. The water in the solution results in the disadvantage that a relatively large amount of ε-caplolactam and colored substances are undesirably mixed into the crystals of the ammonium salt of 11-cyano-undecanoic acid.

Ammonia gas can be introduced into the solution of the crude material in the aromatic hydrocarbon solvent by any conventional method. For example, the ammonia gas can be directly blown into the solution or into a space formed between the upper surface of the solution in a closed vessel and an inside wall surface of the vessel. In another method, the solution is fed into a reaction column wherein the solution is brought into contact with ammonia gas which is also introduced into the column in the same or opposite flow direction with respect to the flow direction of the solution. The ammonia gas may be diluted with an inert gas, for example, nitrogen gas.

The ammonium gas is preferably introduced into the solution of the crude material in a mole ratio of 0.5 to 2.0, with respect to the sum of the amounts in moles of acid substances in the solution of the crude material. The use of the ammonia gas in a mole ratio larger than 2.0 results in no technical benefit and in an economic disadvantage. If the ammonia gas is introduced in a mole ratio smaller than 0.5 into the crude material solution, it results in a low recovery yield of the ammonium salt of 11-cyano-undecanoic acid.

Ammonia gas is introduced into the solution of the crude material at a temperature lower than a melting point of the ammonium salt of 11-cyano-undecanoic acid, preferably, 60°C or lower, more preferably, between 15° and 60°C. If ammonia gas is introduced at a temperature exceeding the melting point of the ammonium salt of 11-cyano-undecanoic acid, the ammonium salt is molten and forms a separate layer located under the solution layer of the crude material. The impurities in the solution of the crude material tend to move from the solution layer into the melt layer. Accordingly, the crystals of the ammonium salt contain a large amount of the impurities. The introduction of ammonia gas at a temperature lower than 15°C results in no benefit and sometimes tends to contaminate the cyrstals of the ammonium salt of 11-cyano-undecanoic acid with the colored substances from the crude material.

It is preferable to introduce ammonia gas at such a rate that the conversion of 11-cyano-undecanoic acid to its ammonium salt is completed within 60 minutes, more preferably, within, 15 minutes. An introducing time of ammonia gas longer than 60 minutes results in an economical disadvantage and in undesirable by-reactions. That is, by the side reactions, other component compounds than 11-cyano-undecanoic acid, for example, cyclohexanone, are decomposed or deteriorated in quality. The other component compounds are usable as materials for the chemical industry.

When ammonia gas is introduced into the crude material solution under the above-mentioned preferable conditions, a major portion (86 – 96% by weight) of 11-cyano-undecanoic acid existing in the crude oil prepared from 1,1'-peroxy-dicyclohexylamine is converted into its ammonium salt and crystallized to form a slurry-like mixture. The separation of the ammonium salt is preferably completed at a temperature between 10° and 35°C. If the crystallizing is carried out at a temperature higher than 35°C, a minor portion of the ammonium salt of 11-cyano-undecanoic acid remains dissolved in the solvent and can not crystallize. This results in somewhat of a decrease in the recovery yield of the ammonium salt of 11-cyano-undecanoic acid. Accordingly, if ammonia gas is introduced into the crude material solution at a temperature higher than 35°C, after the complete introducing, the resultant slurry is preferably cooled to a temperature between 10° and 35°C. In this temperature range, the ammonium salt of 11-cyano-undecanoic acid can be crystallized and recovered in an amount corresponding to 95% or more of the original amount of 11-cyano-undecanoic acid in the crude material. Also, in the temperature range between 10° and 35°C, the crystallization of the ammonium salt of 11-cyano-undecanoic acid goes at a high velocity. Accordingly, the slurry containing the ammonium salt crystals can be subjected to the separating step immediately when the slurry attains the temperature range between 10° and 35°C, without the slurry standing for a long time. The separation of the crystals from the slurry can be effected by any conventional separating method, for example, either filtering or centrifuging.

The special solvent of the present invention for the crude material is also useful for completely washing the separated crystals of the ammonium salt of 11-cyano-undecanoic acid, because the solvent can dissolve away the impurities and the colored substances mixed into the crystals but does not dissolve a substantial amount of the crystals.

The ammonium salt of 11-cyano-undecanoic acid prepared by the method of the present invention has a mole ratio of 11-cyano-undecanoic acid ingredient to ammonium ingredient of approximately 1:½. This can be confirmed by way of alkali titration. 11-cyano-undecanoic acid can be utilized in the form of its ammonium salt for various uses. However, if it is necessary, the ammonium salt can be easily converted to free 11-cyano-undecanoic acid by bringing the ammonium salt into contact with a diluted aqueous solution of a mineral acid, for example, hydrochloric acid and sulfuric acid. Since the free 11-cyano-undecanoic acid is substantially insoluble in the diluted mineral acid aqueous solution, the conversion of the ammonium salt to the free acid and the recovery of the free acid are carried out quantitatively.

By effecting the method of the present invention, crystals of the ammonium salt of 11-cyano-undecanoic acid having a purity of at least 92% by weight, generally, 99% by weight or more, can be obtained in a recovery yield of more than 95%, generally, 95 to 98% based on the amount by mole of 11-cyano-undecanoic acid in the crude material. If it is desired, the ammonium salt of 11-cyano-undecanoic acid can be converted to free 11-cyano-undecanoic acid by a diluted mineral acid aqueous solution.

The features and advantages of the method of the present invention are further illustrated by the examples set forth below, which are not intended to limit the scope of the present invention. In the examples, 2% solution Hazen number was determined by the following method.

A 2% solution of the ammonium salt of 11-cyano-undecanoic acid to be tested was prepared by dissolving 2.0 g of the crystalline ammonium salt of 11-cyano-undecanoic acid in methyl alcohol and the solution was adjusted to the volume of 100 ml by adding a necessary amount of methyl alcohol.

Separately, a standard Hazen solution was prepared by dissolving 1.246 g of potassium chloroplatinate (containing 500 mg of platinum) and 100 g of cobalt chloride hexahydrate into 100 ml of hydrochloric acid and adjusting the solution to a volume of 1000 ml by adding water. The standard Hazen solution has a Hazen number of 500. For example, a solution which has been prepared by diluting the standard Hazen solution with water to a volume of 10 times that of the original standard Hazen solution, has a Hazen number of 50. The standard Hazen solution has an absorbance of 0.674 at a wave length of 457 m$\mu$, when measured using an optical glass cell having a 5 cm thickness.

The absorbance (As) of the 2% solution of the ammonium salt of 11-cyano-undecanoic acid was measured by the same method as that for the standard Hazen solution. The 2% solution Hazen number was determined in accordance with the following equation:

2% solution Hazen number = As × (500/0.674):

EXAMPLE 1

A crude oil was prepared by thermally cracking 1,1'-peroxy-dicyclohexyl amine at a temperature of 500°C in accordance with the method disclosed in German published application No. 2,038,956. The crude oil was dissolved in toluene to prepare a solution containing therein 10.8% by weight of 11-cyano-undecanoic acid, 1.19% by weight of $\epsilon$-caprolactam and 4.31% by weight of cyclohexanone, and having a concentration of the sum of acid substances of 0.576 meq/g.

A 400 g solution of the crude oil was charged into a flask located in a water bath and having a glass conduit for blowing ammonia gas thereinto and a stirrer. The solution was stirred by the stirrer and 5.66 liters of ammonia gas were blown into the solution through the glass conduit in 11 minutes. The amount of ammonia used was equal in moles to the sum of the acid substances in the crude oil solution. The 11-cyano-undecanoic acid was converted to its ammonium salt with generation of heat, resulting in a slurry wherein the crystallized ammonium salt of 11-cyano-undecanoic acid was suspended in toluene. The temperature of the slurry reached 33°C. Without cooling the slurry it was filtered under suction through a glass filter. The filtered crystals were washed with 50 ml of toluene and, then, dried. The dried crystals were in an amount of 43.6 g and had a 2% solution Hazen number of 62. It was determined by way of alkali titration that the crystals contained 95.7% by weight of 11-cyano-undecanoic acid, and the 11-cyano-undecanoic acid was in the form of its ½ mole ammonium salt. Therefore, it was calculated that the crystals contained 99.5% by weight of ½ mole ammonium salt of 11-cyano-undecanoic acid, and that 11-cyano-undecanoic acid was recovered from the crude oil in a yield of 96.6%.

EXAMPLE 2

Operations identical to those in Example 1 were repeated except that the toluene solution of the crude oil was maintained at a temperature between 45° and 47°C during the blowing period of ammonia gas. The resultant slurry was cooled to a temperature of 20°C for 11 minutes. The resultant crystals were in an amount of 43.65 g and had a 2% solution Hazen number of 36. The content of 11-cyano-undecanoic acid in the crystals was 95.5% by weight determined by way of chromatography, which value was very close to 95.4% by weight determined by way of alkali titration. From the alkali titration, it was observed that the 11-cyano-undecanoic acid is in the form of its ½ mole ammonium salt. Accordingly, it was calculated that the content of the ½ mole ammonium salt of 11-cyano-undecanoic acid in the crystals was 99.3%, and 11-cyano-undecanoic acid was recovered from the crude oil in an yield of 96.4%. Further, it was observed that the crystals contained therein a very small amount, 0.03% by weight, of $\epsilon$-caprolactam.

EXAMPLES 3 THROUGH 6

Operations identical to those in Example 2 were repeated four times except that the mole ratio of the ammonia blown into the crude oil solution to the sum of acid substances in the crude oil and the blowing temperature of the ammonia gas were varied as set forth as indicated in Table 1. The results are also illustrated in Table 1.

toluene, was treated with ammonia blown thereinto at a mole ratio as illustrated in Table 2 at a blowing temperature also illustrated in the table for 11 minutes. The resultant slurry was cooled to a temperature of 20°C. The crystallized ammonium salt of 11-cyano-undecanoic acid was separated by filtration, washed with toluene and, then, dried. The results are indicated in Table 2.

Table 2

| Example No. | Mole ratio of NH$_3$ to acid substances | Blowing temperature of ammonia gas (°C) | Product |||||
|---|---|---|---|---|---|---|---|
| | | | Yield (g) | Content of CUDA (% by weight) | Content of CUDA½NH$_3$ (% by weight) | Content of $\epsilon$-caprolactam (% by weight) | 2% solution Hazen number | Recovery (% by mole) |
| 7 | 1.00 | 42 – 50 | 53.9 | 96.0 | 99.9 | 0.1 | 64 | 95.8 |
| 8 | 1.51 | 52 – 58 | 54.1 | 95.7 | 99.5 | 0.1 | 84 | 95.9 |

EXAMPLES 9 THROUGH 11 and

COMPARISON EXAMPLES 1 THROUGH 3

In each of the Examples 9 through 11, the same crude oil as used in Example 1 was dissolved in an aromatic solvent illustrated in Table 3 to prepare a 400 g solution containing therein 10.2% by weight of 11-cyano-undecanoic acid, 1.13% by weight of $\epsilon$-caprolactam and 3.16% by weight of cyclohexanone, and having a content of the sum of acid substances of 0.586 meq/g.

The solution was treated with ammonia gas blown into the solution at a mole ratio of ammonia to the sum of acid substances in the solution and at a temperature illustrated in Table 3 for 12 minutes. The resultant slurry was cooled to 20°C and filtered and the resultant crystals were washed and dried. The results are illus- Table 1

| Example No. | Mole ratio of NH$_3$ to acid substances | Blowing temperature of ammonia gas | Product ||| Recovery (% by mole) |
|---|---|---|---|---|---|---|
| | | | Content of CUDA(*)1 (% by weight) | Content of CUDA½NH$_3$ (*)2 (% by weight) | 2% solution Hazen number | |
| 3 | 0.88 | 44 – 45 | 95.7 | 99.5 | 91 | 95.7 |
| 4 | 1.00 | 45 – 46 | 95.8 | 99.7 | 30 | 97.9 |
| 5 | 1.40 | 40 – 49 | 95.2 | 99.0 | 35 | 97.7 |
| 6 | 1.74 | 40 – 47 | 95.5 | 99.3 | 40 | 95.4 |

Note:
(*)1 CUDA 11-cyano-undecanoic acid
(*)2 CUDA½NH$_3$ ½mole ammonium salt of 11-cyano-undecanoic acid

EXAMPLES 7 and 8

In each of the Examples 7 and 8, in accordance with the operations in Example 1, 450 g of a crude oil solution containing therein 12.0% by weight of 11-cyano-undecanoic acid, 4.07% by weight of cyclohexanone and 1.22% by weight of $\epsilon$-caprolactam, and having a content of the sum of acid substances of 0.656 meq/g in trated in Table 3. In each of the Comparative Examples 1 through 3, the same operations as in Example 9 were carried out, except that the crude oil was dissolved in a non-aromatic solvent as illustrated in Table 3 and that the blowing of ammonia was carried out at a mole ratio and at a temperature as illustrated in Table 3. The results are indicated in Table 3.

Table 3

| Example No. | Solvent | Mole ratio of NH$_3$ to acid substances | Blowing temperature of ammonia gas (°C) | Product |||| Recovery (% by mole) |
|---|---|---|---|---|---|---|---|---|
| | | | | Content of CUDA (% by weight) | Content of CUDA½NH$_3$ (% by weight) | Content of $\epsilon$-caprolactam (% by weight) | 2% solution Hazen number | |
| Examples 9 | Benzene | 1.0 | 44 – 46 | 96.0 | 99.9 | 0.02 | 27 | 95.7 |
| 10 | Mixed xylene | 1.0 | 45 – 46 | 94.2 | 98.0 | 0.18 | 208 | 97.1 |
| 11 | Ethylbenzene | 1.74 | 40 – 51 | 89.2 | 92.8 | 0.80 | 120 | 98.3 |
| Compa- 1 | Cyclo- | 1.0 | 41 – 46 | 77.8 | 80.7 | 3.32 | 1350 | 99.4 |

Table 3-continued

| Example No. | Solvent | Mole ratio of NH₃ to acid substances | Blowing temperature of ammonia gas (°C) | Product Content of CUDA (% by weight) | Content of CUDA½NH₃ (% by weight) | Content of ε-capro-lactam (% by weight) | 2% solution Hazen number | Recovery (% by mole) |
|---|---|---|---|---|---|---|---|---|
| rative Examples 2 | hexane Ligroin | 1.0 | 43 – 50 | 80.0 | 83.2 | 2.56 | 1345 | 99.2 |
| 3 | Chloroform (*) | 1.7 | 28 – 44 | 68.7 | 71.5 | — | 190 | 29.0 |

Note:
(*):water-saturated chloroform

COMPARATIVE EXAMPLE 4

The same crude oil as used in Example 1 was distilled at a temperature not exceeding 150°C under a reduced pressure of 20 mmHg to eliminate cyclohexanone therefrom. The resultant crude 11-cyano-undecanoic acid included therein 72.0% by weight of 11-cyano-undecanoic acid and 6.8% by weight of ε-caprolactam. 125 g of the crude 11-cyano-undecanoic acid was dissolved in 60 ml of methyl alcohol and the solution was sprayed into 1100 ml of water at a temperature of 18°C for 18 minutes while vigorously stirring the water. The resultant aqueous slurry was filtered while sacking and the filtered crystals were washed with 300 ml of water and, then, dried. 107.2 g of crystals were obtained with a recovery yield of 98.6% by weight. The crystals contained 82.8% by weight of 11-cyano-undecanoic acid and 0.52% by weight of ε-caprolactam and had a 2% solution Hazen number of 2840.

COMPARATIVE EXAMPLE 5

The same crude 11-cyano-undecanoic acid as used in Comparison Example 4 in an amount of 150g was dissolved in 850g of an ammonia aqueous solution containing 5.8% by weight of ammonia. The solution was subjected three times to extraction with 333g of chloroform at room temperature to remove impurities from the solution. Thereafter, the solution was cooled to a temperature of 10°C. No crystal was observed in the cooled solution. In order to promote the crystallization of 11-cyano-undecanoic acid, 1 g of pure 11-cyano-undecanoic acid was added as a crystal nucleus into the solution, and the solution was maintained at a temperature of 4°C for 14 hours. The resultant slurry was filtered while sucking, and the filtered crystals were washed with 30 ml of a cold aqueous ammonia solution and dried for 1 night under vacuum. The crystals were obtained in an amount of 88.6g, and had a content of 11-cyano-undecanoic acid of 90.2% by weight which was determined by alkali titration. In the crystals, 11-cyano-undecanoic acid and ammonia was bonded in a mole ratio of 1:0.74. Accordingly, the crystals had a relatively low content of ammonium salt of 11-cyano-undecanoic acid of 95.6% and a relatively low recovery yield of 73.3% based on the sum of the weight of 11-cyano-undecanoic acid in the crude oil and the weight of the crystal nucleus. Further, it was determined that the crystals contained 0.05% by weight of ε-caprolactam and had a 2% solution Hazen number of 117.

COMPARATIVE EXAMPLE 6

40 g of the same crude 11-cyano-undecanoic acid were dissolved in 500 g of water-saturated chloroform at a temperature of 45°C. At this temperature, 5.5 liters of ammonia gas was introduced into the chloroform solution. The solution was maintained at room temperature for 2 hours. However, no crystal was created in the solution. Then the solution was cooled to a temperature of 5.5°C and maintained at this temperature for 1 night. The resultant crystals were separated from the solution by suction filtration and the filtered crystals were washed with 40 ml of chloroform. In the suction filtration, it was observed that the filtration of the crystals required a long time due to the crystals being too small in size. The crystals were dried, and the dried crystals had an amount of 25.3g and a 2% solution Hazen number of 82. By way of alkali-titration, it was observed that the crystals contained 95.7% by weight of 11-cyano-undecanoic acid and the 11-cyano-undecanoic acid bonded with ammonia in a mole ratio of 1:½. Accordingly, the crystals contained 99.5% by weight of ½ mole ammonium salt of 11-cyano-undecanoic acid and a recovery yield of 84.1% based on the weight of 11-cyano-undecanoic acid in the crude oil.

What we claim is:
1. A method for isolating 11-cyano-undecanoic acid in the form of its ammonium salt from a crude oil containing therein 11-cyano-undecanoic acid obtained by thermally cracking 1,1'-peroxy-dicyclohexyl amine at a temperature between 300° and 1000°C, comprising the steps of:
  dissolving said crude oil into an organic solvent consisting of at least one aromatic hydrocarbon having 6 to 8 carbon atoms to prepare a solution containing 5 to 30% by weight of 11-cyano-undecanoic acid;
  introducing ammonia gas into the above-prepared solution to convert the dissolved 11-cyano-undecanoic acid to its ammonium salt crystals, said ammonia gas being introduced into said solution of said crude oil in an amount of 0.5 to 2.0 times by mole the sum of the contents of the acid substances existing in said crude oil, said introducing of ammonia gas being carried out at a temperature not higher than the melting point of said ammonium salt of 11-cyano-undecanoic acid; and
  separating said crystals of ammonium salt of 11-cyano-undecanoic acid from said solution.
2. A method as set forth in claim 1, wherein said organic solvent is selected from the group consisting of benzene, toluene, xylene, ethyl benzene and mixtures of two or more of the above-mentioned compounds.

3. A method as set forth in claim 1, wherein said introducing temperature of ammonia gas is between 15° and 60°C.

4. A method as set forth in claim 1, wherein said introducing of ammonia gas is completed within 60 minutes.

5. A method as set forth in claim 4, wherein said introducing time of ammonia gas is completed within 15 minutes.

6. A method as set forth in claim 1, wherein said crystallizing of said ammonium salt of 11-cyano-undecanoic acid is completed at a temperature between 10° to 35°C.

7. A method as set forth in claim 1, wherein said separating of said crystallized ammonium salt of 11-cyano-undecanoic acid is carried out by mechanical separation selected from the group consisting of filtering and centrifuging.

8. A method as set forth in claim 1, further comprising converting said ammonium salt of 11-cyano-undecanoic acid into free 11-cyano-undecanoic acid by bringing it into contact with an acid aqueous solution.

* * * * *